US006922592B2

(12) United States Patent
Thompson et al.

(10) Patent No.: US 6,922,592 B2
(45) Date of Patent: Jul. 26, 2005

(54) IMPLANTABLE MEDICAL DEVICE CONTROLLED BY A NON-INVASIVE PHYSIOLOGICAL DATA MEASUREMENT DEVICE

(75) Inventors: David L. Thompson, Andover, MN (US); Daniel R. Greeninger, Coon Rapids, MN (US); Steven D. Goedeke, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 92 days.

(21) Appl. No.: 09/825,909

(22) Filed: Apr. 4, 2001

(65) Prior Publication Data

US 2001/0047194 A1 Nov. 29, 2001

Related U.S. Application Data

(60) Provisional application No. 60/194,512, filed on Apr. 4, 2000.

(51) Int. Cl.[7] ............................................... A61N 1/362
(52) U.S. Cl. ............................................ 607/59; 607/4
(58) Field of Search ......................... 128/903; 600/522; 607/32, 59, 60

(56) References Cited

U.S. PATENT DOCUMENTS

| | | | |
|---|---|---|---|
| 4,871,351 A | * 10/1989 | Feingold | 604/66 |
| 5,113,859 A | 5/1992 | Funke | 128/419 PG |
| 5,193,540 A | * 3/1993 | Schulman et al. | 128/419 R |
| 5,487,752 A | * 1/1996 | Salo et al. | 607/17 |
| 5,540,727 A | * 7/1996 | Tockman et al. | 607/18 |
| 5,562,707 A | * 10/1996 | Prochazka et al. | 607/2 |
| 5,683,432 A | 11/1997 | Goedeke et al. | 607/32 |
| 5,724,025 A | * 3/1998 | Tavori | 340/573.1 |
| 5,843,139 A | 12/1998 | Goedeke et al. | 607/32 |
| 5,904,654 A | 5/1999 | Wohltmann et al. | 600/481 |
| 5,941,837 A | * 8/1999 | Amano et al. | 600/595 |
| 5,964,701 A | 10/1999 | Asada et al. | 600/300 |
| 6,155,120 A | 12/2000 | Taylor | 73/862.046 |
| 6,167,310 A | 12/2000 | Grevious | 607/32 |
| 6,200,265 B1 | 3/2001 | Walsh et al. | 600/300 |
| 6,201,993 B1 | 3/2001 | Kruse et al. | 607/30 |
| 6,470,199 B1 | * 10/2002 | Kopotic et al. | 600/344 |

* cited by examiner

*Primary Examiner*—Angela D. Sykes
*Assistant Examiner*—Frances P. Oropeza
(74) *Attorney, Agent, or Firm*—Paul H. McDowall; Girma Wolde-Michael

(57) ABSTRACT

The operational and functional aspects of one or more IMDs is controlled by physiological data acquired from an external device. Various externally deployed devices collect vital signals for transmission to the IMD. Upon receipt of the signals the IMD cooperatively modifies therapy and diagnostic procedures to be substantially compliant with the received signals. Further, the IMD may store some of the signals for future follow-up or patient data management as needed.

8 Claims, 6 Drawing Sheets

US 6,922,592 B2

IMPLANTABLE MEDICAL DEVICE CONTROLLED BY A NON-INVASIVE PHYSIOLOGICAL DATA MEASUREMENT DEVICE

This application claims benefit of Ser. No. 60/194,512 dated Apr. 4, 2000.

FIELD OF THE INVENTION

The present invention generally relates to medical devices. Specifically, the invention relates to an apparatus and method whereby an implantable medical device (IMD) receives data from an external physiological signal sensor and utilizes the information to initiate, control, modify or program the delivery of therapy or store the data for later follow-up retrieval and diagnostic review of a patient. More specifically, the invention provides a dynamic closed loop self monitoring system in which one or more external medical devices measure physiological data such as blood pressure, cardiac output and other vital signs and transmit these measurements to the IMD to thereby provoke a response based on the transmitted signals.

BACKGROUND OF THE INVENTION

Analysis of physiological signals can provide clinicians with highly sensitive and accurate indicators to help identify, diagnose and monitor a variety of medical conditions.

The sensing of physiological data such as, for example, cardiac output is of great benefit for the controlled treatment and diagnosis of numerous diseases. Chronically implantable sensors of various types are currently used in treating and monitoring various disease states. Some typical examples of implantable sensors that have been utilized include pressure, oxygen saturation, flow sensors, microphones, intracardiac impedance and similar other implantable medical devices.

There are various externally and internally installed medical devices that monitor physiological signals to provide clinicians accurate information on the medical condition of patients. Under current practice, implanted device sensors are used in conjunction with implanted devices such as pacemakers, defibrillators, neurological stimulators, drug delivery systems and the like. While the functional and technological aspects of these implanted sensors have improved over the years, there remain significant operational and maintenance/reliability problems to overcome. For example, implanted sensors are prone to tissue overgrowth/fibrosis which may limit or interfere with proper/reliable signal acquisition. Similarly, power depletion, current drain, long term signal stability and similar problems associated with chronic use pose various challenges in the successful and long term implementation of implantable sensors.

External sensing systems are also implemented to monitor various vital signs and physiological conditions of a patient. For example, Peripheral Arterial Tone (PAT) is an important signal relating to peripheral vascular responses to automatic nervous system activity. The PAT measures arterial pulse volume changes in the finger tip which may mirror changes or anomalies in automatic nervous system activity and their related vascular events. Other external sensing systems include the finger cuff for blood pressure and the auto-inflating cuff for periodic blood pressure measurement.

One of the advantages of externally implemented sensor over implanted sensors is the option to change, modify or upgrade without an invasive medical procedure on the patient. Further operational efficiency relating to adjustments, maintenance and other conditional adaptability favor external sensors.

Accordingly, there is a need to enable a cooperation between an IMD and external sensors to overcome some of the problems associated with implanted sensors.

SUMMARY OF THE INVENTION

One aspect of the present invention includes the use of externally deployed medical devices to provide medical data to one or more IMDs, to thereby influence the operations of the IMD vis-à-vis the dispensation of therapy including diagnoses.

Another aspect of the invention provides the control of one or more IMDs on the basis of medical information gathered from externally mounted devices. Specifically, one or more sensors specialized to sense certain physiological condition are implemented in wireless communications with the IMD. The operations of the IMD such as delivery of therapy or diagnostic evaluation of the patient condition is substantially controlled by the input from the physiological data collected by the external device.

DETAILED DESCRIPTION OF THE EMBODIMENTS

The present invention provides an IMD or diagnostic device that is in data communication with an external medical device. The external medical device transmits medical data to the IMD, which data is used, inter alia, to initiate, control, modify the delivery of therapy by the IMD. Further, the medical data from the external device may be stored in the IMD for later follow-up, retrieval and diagnostic review. Such IMD medical devices include implantable cardiac pacemakers, cardioverter/defibrillators, pacemaker/cardioverter/defibrillators, drug deliver systems, cardiomyostimulators, cardiac and other physiologic monitors, electrical stimulators including nerve and muscle stimulators, deep brain stimulators, and cochlear implants, and heart assist devices or pumps, etc.

Figure 1A:
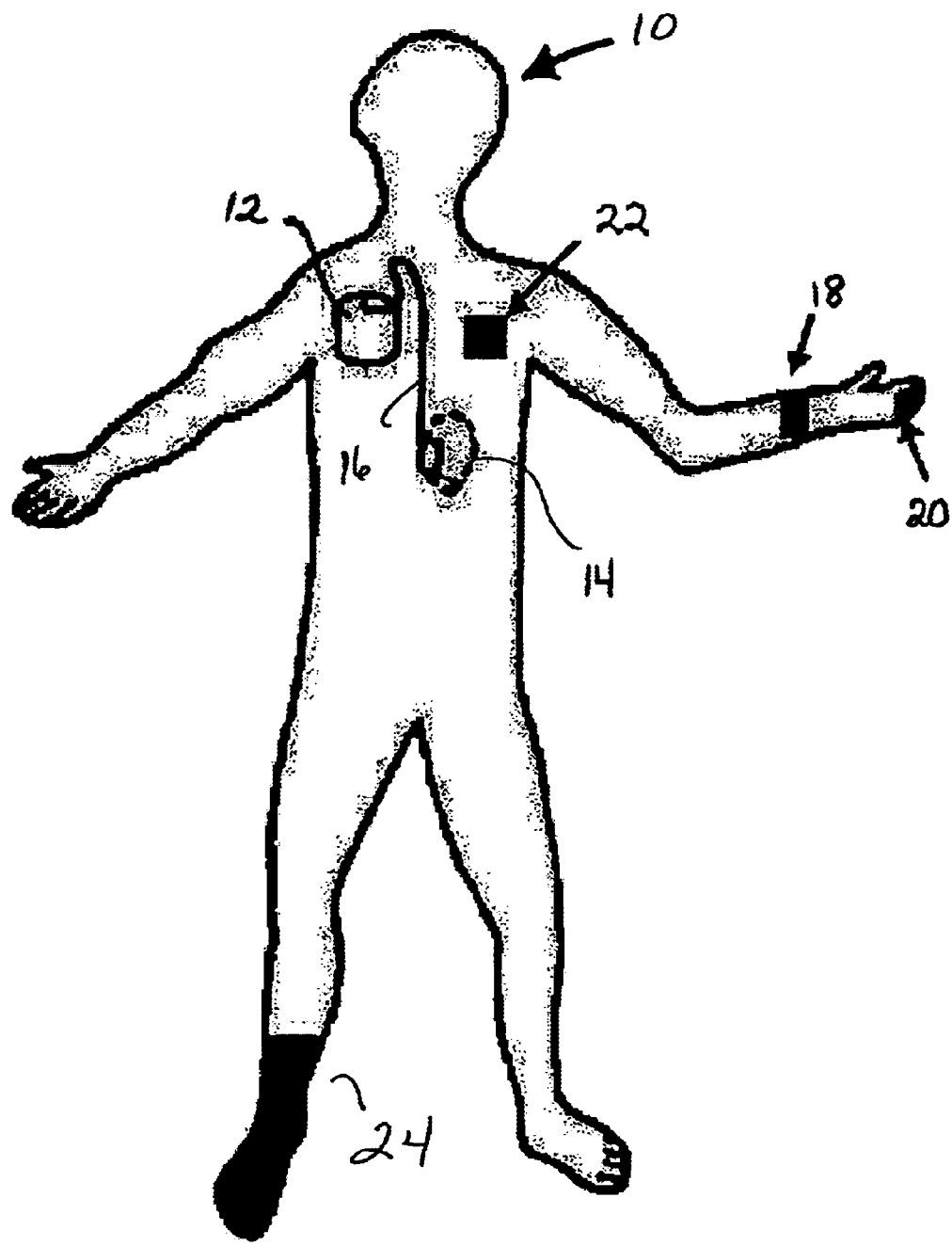
FIG. 1A is a representation of the implementation of the present invention wherein a patient with at least one IMD is fitted with various external sensors being in data communications with the pacemaker.

FIG. 1A represents patent 10 with one or more implantable medical devices IMD 12. In this representative sample, IMD 12 is one of the many cardiac devices delivering a pulse to heart 14 via lead 16. IMD 12 is in data communications with various externally mounted devices equipped with various sensors. Without limitations, the sensors include wristwatch sensor 18, ring sensor 20, patch sensor 22 and sensor sock 24. As is disclosed in FIG. 1B, these externally mounted devices are in operable wireless data communication with IMD 12.

Figure 1B:
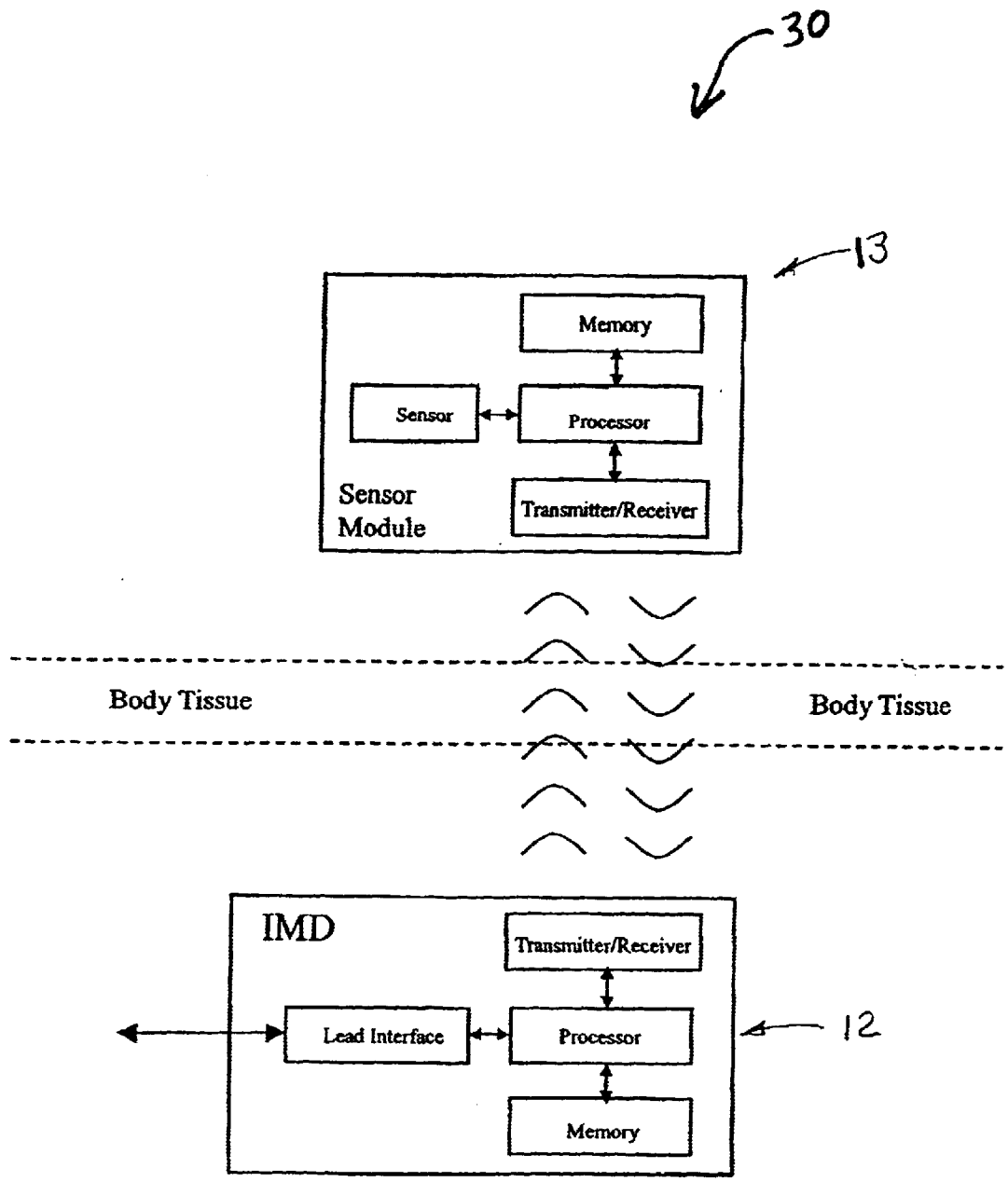
FIG. 1B is a block diagram representing the wireless data transmission scheme in accordance with the invention.

Referring to FIG. 1B, the wireless communication system in accordance with the present invention is shown. Specifically, wireless system 30 is implemented in any one of the external devices 13 to provide communication with IMD 12 is disclosed. More specifically, the system implements wireless communication schemes and processes disclosed in U.S. Pat. No. 5,113,859 to Funke, U.S. Pat. No. 5,683,432 to Goedeke et al, U.S. Pat. No. 5,843,139 to Goedeke et al, U.S. Pat. No. 6,167,310 to Grevious, U.S. Pat. No. 6,200,265B1 to Walsh et al, and U.S. Pat. No. 6,201,993B1 to Kruse et al, all incorporated herein by reference in their entireties. The wireless communication scheme as illustrated, is provided with a sensor module that includes a sensor in bidirectional communication with a memory, a processor and a transmitter/receiver at the externally mounted device 13. The external sensor module transmits the physiological data to the IMD over a communication channel including RF signals.

Figure 2:
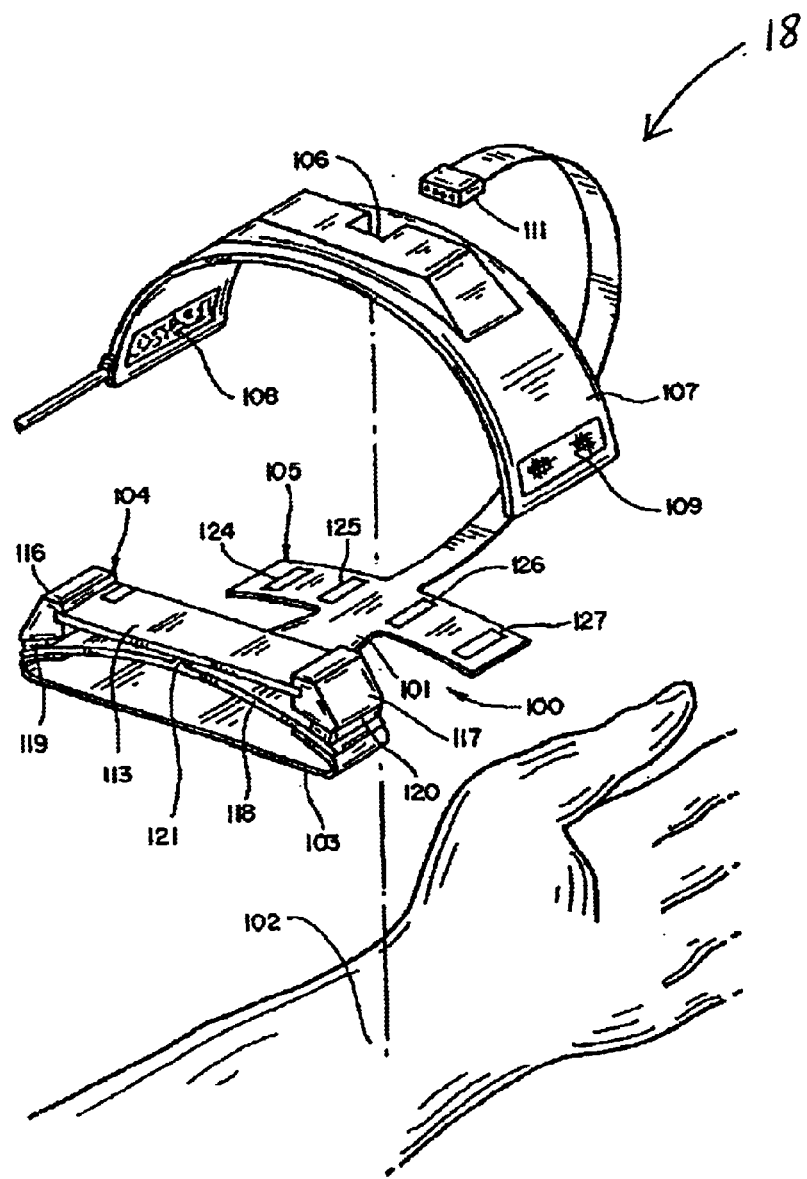
FIG. 2 is a partially exploded view of a blood pressure sensing unit mounted on a wrist in accordance with one embodiment of the invention.

Referring now to FIG. 2, a wrist-wearable unit 18 includes an assembly 100 which further includes a support member 101 placed on the patient's wrist 102 with a suitable adhesive 103 on the underside of member 101. The assembly includes an exciter 104 and a detector 105 mounted on the support member 101. The assembly 100 may be further held in place by cover 107 which includes a recess 106 for the exciter 104. Cover 107 is wrapped around the patient's wrist and held in place by Velcro hooks 108 and Velcro latches 109. Electrical connections (not shown) are made to the detector and sensor by thin conductive film lead formed in the support member 101. The leads terminate in a connector 111. Thus, the exciter and detector are maintained in spaced relationship in contact with the patient by support member 101.

As disclosed in U.S. Pat. No. 5,904,654 to Wohltmann et al, incorporated herein by reference in its entirety, unit 18 includes an exciter and a detector mounted on a common support for inducing perturbations into the body and detecting the perturbations after they travel a distance through the body in order to detect a hemoparameter. Unit 18 is adapted to be in telemetry or wireless communication with implanted medical device (IMD) 12 such that IMD 12 receives physiological parameters that are measured by unit 18 on a continuous basis. The assembly of unit 18 may be held in intimate contact with the body of patient 10 by means of an adhesive, adhesive tape, vacuum or pressure or equivalent. The interface may include gel, fluid, rubber or foam. Thus, unit 18 may be attached to patient 10 in such a way that the overall pressure over the assembly can be varied in a controlled way in order to modify the pressure experience by the underlying tissue. An example would be the case of a single unit assembly for measurement of blood pressure in which the ability to modulate the transmural arterial pressure facilitates determination of the relationship between the velocity of propogation of the excitation along the artery and blood pressure, one of the physical parameters that may be under investigation. This information could be transferred to IMD 12 via the wireless transmission scheme disclosed hereinabove.

Figure 3:
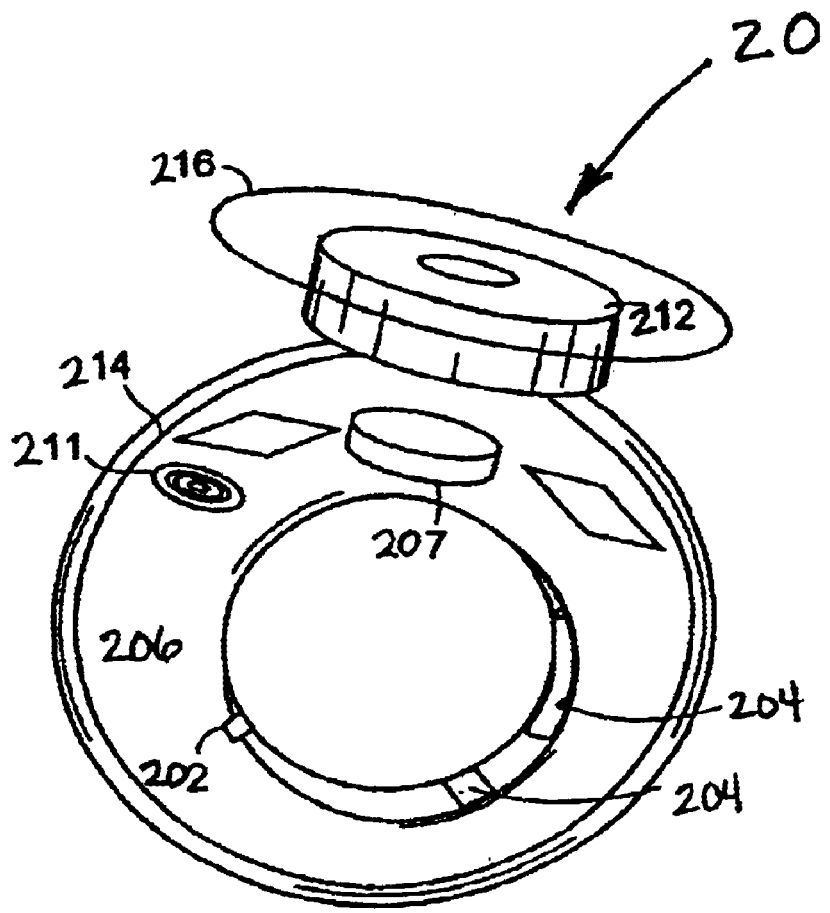
FIG. 3 is a perspective view of a finger ring sensor according to an embodiment of the invention.

Referring now to FIG. 3, finger ring sensor 20 may be worn by patient 10 to monitor various parameters and transmit signals to IMD 12. A finger ring is nonintrusive and can be worn at all times. Even, for example, when taking a shower, people keep wearing rings. Accordingly, finger rings are an appropriate locus for invading patient monitoring sensors and wireless transmitter in order to keep track of the patient twenty-four hours a day. Other articles of apparel may also be used in the manner described below with respect to finger rings.

Referring to FIG. 3 in more detail, consistent with the disclosure in U.S. Pat. No. 5,964,701 to Asada et al incorporated herein by reference in its entirety, finger ring 20 represents a sensor with a wireless transmitter. Specifically, one or more diodes 202 and one or more light emitting diodes 204 are embedded in a ring 210 facing each other inside finger ring 20. LEDs may emit light in the visible or infrared and may be particularly chosen to emit light at one or more specified wavelength, such as the isopiestic wavelength discussed below.

The pulse of patient 10 may be detected as a periodic change in the sensor output. Finger ring 20 may be placed on one of patient 10's fingers. In a preferred embodiment, finger ring 20 is placed on the middle finger, which is not only convenient for wearing the ring, but also suitable for counting pulse. The outer skin of the middle finger is thin, particularly at the sides of the finger, and a digital artery runs right beneath the thin skin. With an appropriate threshold, the sensor detecting the beat produces a pulse train of on-off signals and the pulse train is sent to a transmitter (not shown), contained within electronic module 206, which in a preferred embodiment, is realized as a flexible printed circuit board. When optical sensors are used, interference from the ambient light may corrupt the photo probe signals. As the patient moves, the ambient light coming to the ring photo probe varies, resulting in inconsistent data. A simple approach to preventing ambient light interference is to acquire the signal when all LEDs 204 are turned off and subtract this background effect from the measured signals.

In accordance with an embodiment of the invention, the optical sources which may be LEDs 204 may be modulated and detection may be performed using synchronous detection techniques known to persons to ordinary skill in the art of signal processing. Specifically, as it relates to the present invention, finger ring 20, communicates with implanted device 12 such that data relating to skin temperature, blood flow, blood concentration or pulse rate of patient 12 is transmitted to IMD 12 to thereby initiate a an appropriate diagnostic or therapeutic response/operation by IMD12.

Figure 4:
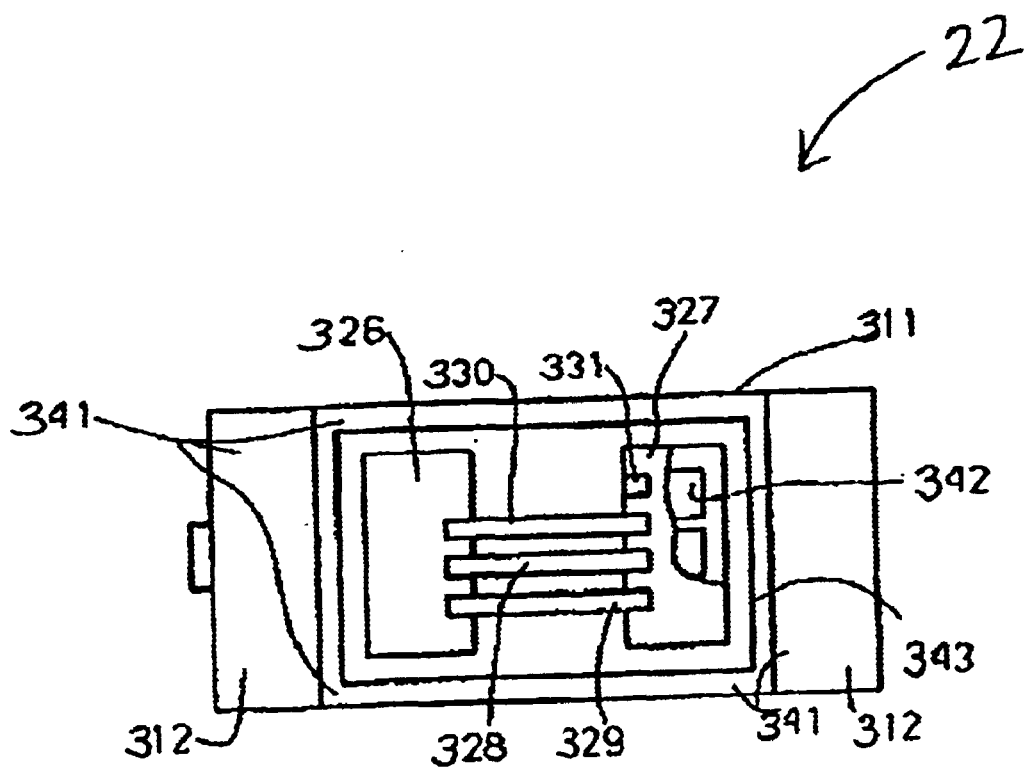
FIG. 4 is a schematic representation of a patch sensor which is in contact with the monitored body.

Referring now to FIG. 4, patch sensor or sensor 22 is shown in contact with the body of patient 10, as disclosed in U.S. Pat. No. 5,724,025 to Tavori, incorporated herein by reference in its entirety. Sensor 22 includes at least two separate electrodes. One electrode is thick 326 while one is substantially thin 327. Electrodes 326 and 327 are in contact with monitored body patient 10 and form a substantial base for mounting single or plurality of sensors. Also shown are mounting means 312 and a position on which an adhesive layer 341 can be implemented in order to allow sensor 22 to be mounted on a measured body surface. For ease of presentation, four sensors are represented: 328, 329, 330 and 331. It is to be understood that more or fewer sensors may be used. As a non limiting example, sensors 328 can measure heart electro potentials for which potential and ground electrodes are needed. Sensor 329 can measure surface conductivity for which different polarity electrodes are needed. Sensors 330 can measure local vascular pressures and use electrodes 327 as a membrane or capacitor plate while sensor 331 can measure temperature and uses electrode 326 as a neat sink. Such an arrangement is not easily achieved, as different sensors may interfere with other sensors' output. By way of a non-limiting example, a sensor which measures surface conductivity 329 forms an electrical short circuiting which will interfere with a sensor measuring electrical potential 328. A switching-coupling element 342 is mounted on the electronic circuit 343, thus providing means to alternately connect and disconnect sensors which may interfere with each other. The sensors provide their output in any convenient values such as voltage, current, frequency, capacitance, inductance, resistance, TTL and the like. As a non-limiting example, a thermocouple can indicate changes in external temperature through a change in voltage. Similarly, a piezoelectric crystal can be used to measure local pressure. By enabling the managing physician to define the type of sensor connected to sensor 22, a measurement of voltage is achieved, however, differently interprinted to different sensors/logics. Furthermore, since the magnitude of these signals may vary by an order of magnitude or more, out of ranging may be implemented to shift results to manageable value ranges.

Similar to sensor 18 and ring sensor 20, patch sensor 22 is adapted to be in data communications with IMD 12. Accordingly, sensor 22 would transmit data relating to vital signs of patient 10 to IMD 12 to thereby initiate control, modify the delivery of therapy or record the data for later follow-up retrieval and diagnostic review.

Figure 5:
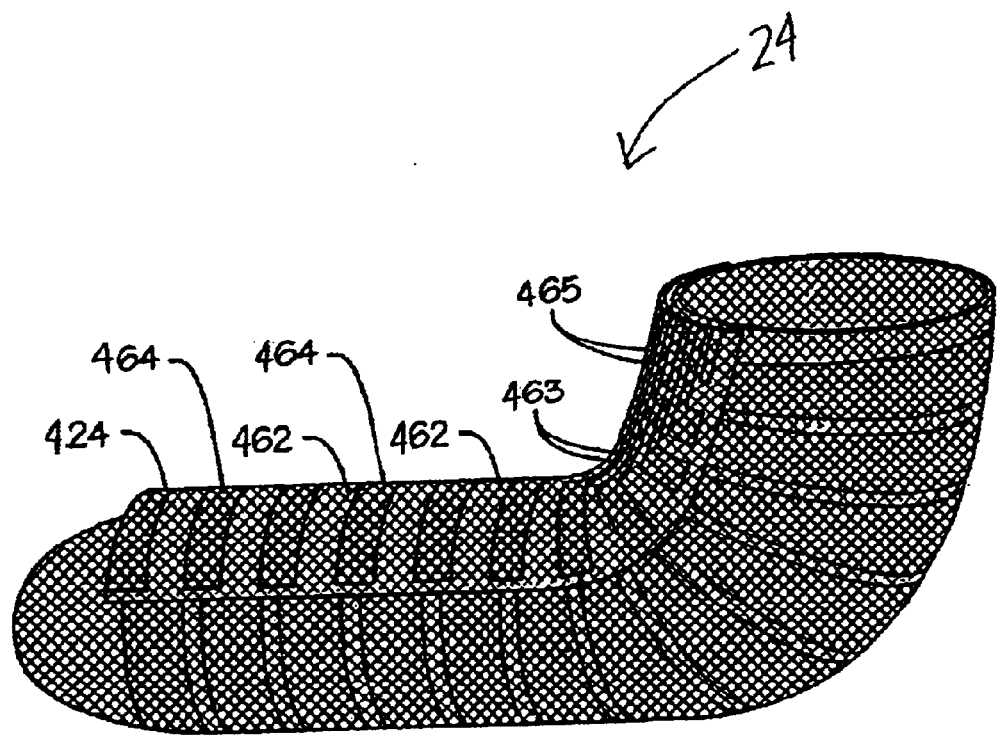
FIG. 5 is a perspective view of a sock incorporating four sensors according to the present invention.

Referring to FIG. 5, sensor sock 24 is shown fitted on the foot of patient 10 in accordance with the disclosure of U.S. Pat. No. 6,155,120 to Taylor, incorporated herein by reference in its entirety. Sensor sock 24 generally includes an array of piezoresistive force sensors that is inserted into a shoe or is incorporated into a sock that may be pulled over a foot. Sensor sock 24 may be implemented for forced sensing and mapping. The device includes an outer tubular raw lead-out tubular lamination 424. Lead-out tubular lamination 424 is made from flextron material having etched through the thickness dimension thereof circumferentially and longitudinally disposed insulating paths 462 and 463 defining laterally disposed longitudinally flag appendages 464 connected to longitudinally disposed lead-out traces 465.

Generally, sensor sock 24 measures pressures exacted on the foot of patient 10. Sock 24 comprises, preferably, a rectangular array of Piezoresistive force sensors encapsulated in a thin polymer package incorporated therein. The sensors are responsive to contact pressures and shear forces directed to the contact plane. The electrical resistance between the pads varies in a predetermined manner as a function of the shear force.

Such a sensor could be used to measure a number of valuable physiological parameters including weight, ankle swelling for edema, and patient activity. Similar to sensors 18, ring sensor 20, and patch sensor 22, sock sensor 24 is adapted to be in data communications with IMD 12. Accordingly, sensor 24 would transmit data relating to vital signs of patent 10 to IMD 12 to thereby initiate control, modify the delivery of therapy or record the data for later follow-up retrieval and diagnostic review.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A system comprising:
    at least one implantable medical device ("IMD" providing therapy delivery, said IMD including a processor controlling the delivery of therapy to a patient; and
    an external sensor module having at least one physiological sensor adapted to operatively couple to a surface portion of a lower peripheral limb of the patient and operational to continuously collect physiological data of the patient wherein said external sensor module continuously transmits the continuously collected physiological data to the IMD;
    wherein said IMD processor processes the physiological data to produce therapy delivery control signals in implementation of dynamic, closed-loop self-monitoring therapy delivery and wherein said external sensor module comprises a sock-based sensor and wherein said sock-based sensor is adapted to collect physiological data including at least one of: a patient weight metric, a patient ankle-swelling metric, a patient activity metric.

2. The system of claim 1 wherein said at least one cardioverter/defibrillator IMD comprises one of: a pacemaker, an implantable cardioverter/defibrillator, a drug delivery system, a nerve stimulator.

3. The system of claim 1 wherein said external sensor module transmits the physiological data to the IMD over a communication channel including RF signals.

4. The system of claim 1 wherein said physiological sensor is a piezoresistive force sensor.

5. A method comprising:
    providing therapy delivery using at least one implantable medical device ("IMD"), said IMD including a processor controlling the delivery of therapy to a patient; and
    continuously collecting physiological data of the patient using an external sensor module having at least one physiological sensor;
    continuously transmitting the physiological data from said external sensor module to the IMD; and
    processing the physiological data to produce one or more therapy delivery control signals in a dynamic, closed-loop, self-monitoring therapy delivery regime wherein said external sensor module comprises a sock-based sensor and wherein said sock-based sensor is adapted to collect physiological data including at least one of; a patient weight metric, a patient ankle-swelling metric, a patient activity metric.

6. A method according to claim 5, wherein said at least one IMD comprises a pacemaker.

7. A method according to claim 5, wherein said external sensor module transmits the physiological data to the IMD over a communication channel including RF signals.

8. A method according to claim 5, wherein said at least one physiological sensor comprises a one of: a pressure sensor, an oxygen saturation sensor, an acceleration sensor, an impedance sensing apparatus.

* * * * *